United States Patent [19]

Zaiger et al.

[11] Patent Number: Plant 6,753

[45] Date of Patent: Apr. 25, 1989

[54] NECTARINE TREE ("MID GLO")

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 143,656

[22] Filed: Jan. 13, 1988

[51] Int. Cl.[4] ..... A01H 5/00

[52] U.S. Cl. ..... Plt./41

[58] Field of Search ..... Plt./41

*Primary Examiner*—James R. Feyrer

[57] ABSTRACT

The new and unique variety relates to a nectarine tree which has the following combination of desirable features:

1. Fruit with a high degree of attractive red skin color.
2. Fruit with good flavor and eating quality.
3. Heavy and regular production of fruit.
4. Having fruit with firm flesh, good shipping and storage quality.
5. Vigorous upright growth.

1 Drawing Sheet

ORIGIN OF THE VARIETY

The present variety of nectarine tree was originated by use in the experimental orchard located at Modesto, Calif., as a first generation cross between a selected nectarine seedling labeled 4E180 and a late maturing nectarine tree of unknown parentage. The female parent labeled 4E180 originated from a group of seedlings grown from open pollinated May Grand (U.S. plant Pat. No. 2,794) nectarine seeds.

ASEXUAL REPRODUCTION OF THE VARIETY

The new variety of nectarine tree was asexually reproduced by budding in the experimental orchard located at Modesto, Calif. and shows that all characteristics are established and transmitted through succeeding propagations and run true to the original tree in all respects.

SUMMARY OF THE VARIETY

The new and distinct variety of nectarine tree which is of large size, vigorous, upright in growth and a regular and productive bearer of large, yellow flesh, clingstone fruit with yellow ground color, overspread with attractive red skin color. The fruit is further characterized by having good flavor and eating quality and the ability to ship to long distant markets, the maturity season being 4 to 5 days before Fantasia Nectarine (nonpatented).

PHOTOGRAPHS OF THE VARIETY

The accompanying color photographic reproductions are of the foliage and fruit of our new variety, with the upper and lower surfaces of the foliage being illustrated and typical specimens of the fruit, an exterior and a sectional view being shown with the stone remaining in place. These photographs were taken shortly after being picked at maturity (hard ripe) and the colors are as nearly true as is reasonably possible in a color presentation of this type.

DESCRIPTION OF THE VARIETY

The botanical details of our new and distinct variety of nectarine tree are based upon observations of specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Production.*—Productive.
- *Density.*—Dense.
- *Bearing.*—Regular.

Trunk:
- *Size.*—Medium stocky.
- *Texture.*—Rough to shaggy.
- *Color.*—Brown to dull brown.

Branches:
- *Size.*—Medium.
- *Texture.*—Medium rough.
- *Lenticels.*—Medium size. Medium number.
- *Color.*—New growth — reddish brown. Old growth — light brown to brown.

Leaves:
- *Size.*—Large. Average length — $5\frac{1}{2}''$ to $6\frac{1}{2}''$. Average width — $1\frac{3}{8}''$ to $1\frac{7}{8}''$.
- *Form.*—Lanceolate. Acutely pointed.
- *Margin.*—Crenate.
- *Color.*—Upper surface — deep green to dark green (27-E-7) to (27-E-8). Lower surface — dull green (27-D-5) to (27-D-6).
- *Texture.*—Smooth.
- *Petiole.*—Medium length. Medium thickness.
- *Glands.*—Reniform. Number varies from 2 to 6. Average number 3. Located on base of leaf blade and upper portion of petiole.

Flower buds:
- *Size.*—Large.
- *Length.*—Medium.

Flowers:
- *Size.*—Large — showy.
- *Pollen.*—Present.
- *Color.*—Pink.
- *Blooming period.*—Mar. 4, 1987 to Mar. 12, 1987. Varies slightly due to climatic conditions.

Fruit:
- *Maturity when described.*—Hard ripe.
- *Date of first picking.*—July 13, 1987.

*Date of last picking.*—July 18, 1987.

*Size.*—Large. Comparatively uniform. Average diameter axially — $2\frac{3}{4}''$ to 3". Average transversely in suture plane $2\frac{3}{4}''$ to 3".

*Form.*—Globose.

*Suture.*—Shallow. Extends from base to apex.

*Ventral surface.*—Rounded.

*Apex.*—Varies from round to slight apexial point.

*Cavity.*—Rounded — slightly elongated in suture plane. Average depth — 7/16". Average breadth — $\frac{3}{4}''$.

*Base.*—Truncate.

Skin:

*Thickness.*—Medium.

*Texture.*—Medium, tenacious to flesh.

*Tendency to crack.*—None.

*Down.*—Wanting.

*Color.*—Yellow ground color (3-A-8) to (4-A-8). Red blush covering most of surface (8-B-8) to (9-B-8).

Flesh:

*Texture.*—Firm and meaty.

*Juice.*—Moderate.

*Ripens.*—Even.

*Flavor.*—sub-acid to mild.

*Aroma.*—Very little.

*Eating quality.*—Good.

*Fibers.*—Few, tender.

*Color.*—Yellow to chrome yellow (4-A-7) to (4-A-8).

Stone:

*Type.*—Clingstone.

*Size.*—Large. Average length — $1\frac{1}{4}''$. Average breadth — 1". Average thickness — $\frac{5}{8}''$.

*Form.*—Ovid.

*Base.*—Straight to slightly rounded.

*Sides.*—Mostly equal.

*Surface.*—Irregularly furrowed toward apex, pitted toward base.

*Apex.*—Acuminate.

*Color.*—Light brown (7-B-5) to (7-C-6).

*Tendency to split.*—Very slight.

Use: Dessert. Market — local and long distance.

Shipping quality: Good.

Storage quality: Good.

The nectarine tree and its fruit herein described may vary in slight detail due to climatic, soil conditions and cultural practices under which the variety may be grown; the present description is that of the variety grown under the ecological condition prevailing at Modesto, Calif.

We claim:

1. A new and distinct variety of nectarine tree characterized by its large size, vigorous, upright growth and a productive and regular bearer of large size, firm, yellow flesh, clingstone fruit, maturing 4 to 5 days before Fantasia Nectarine (non-patented); the fruit is further characterized by its good flavor and eating quality; its attractive red skin color and its ability to store and ship to long distant markets.

* * * * *

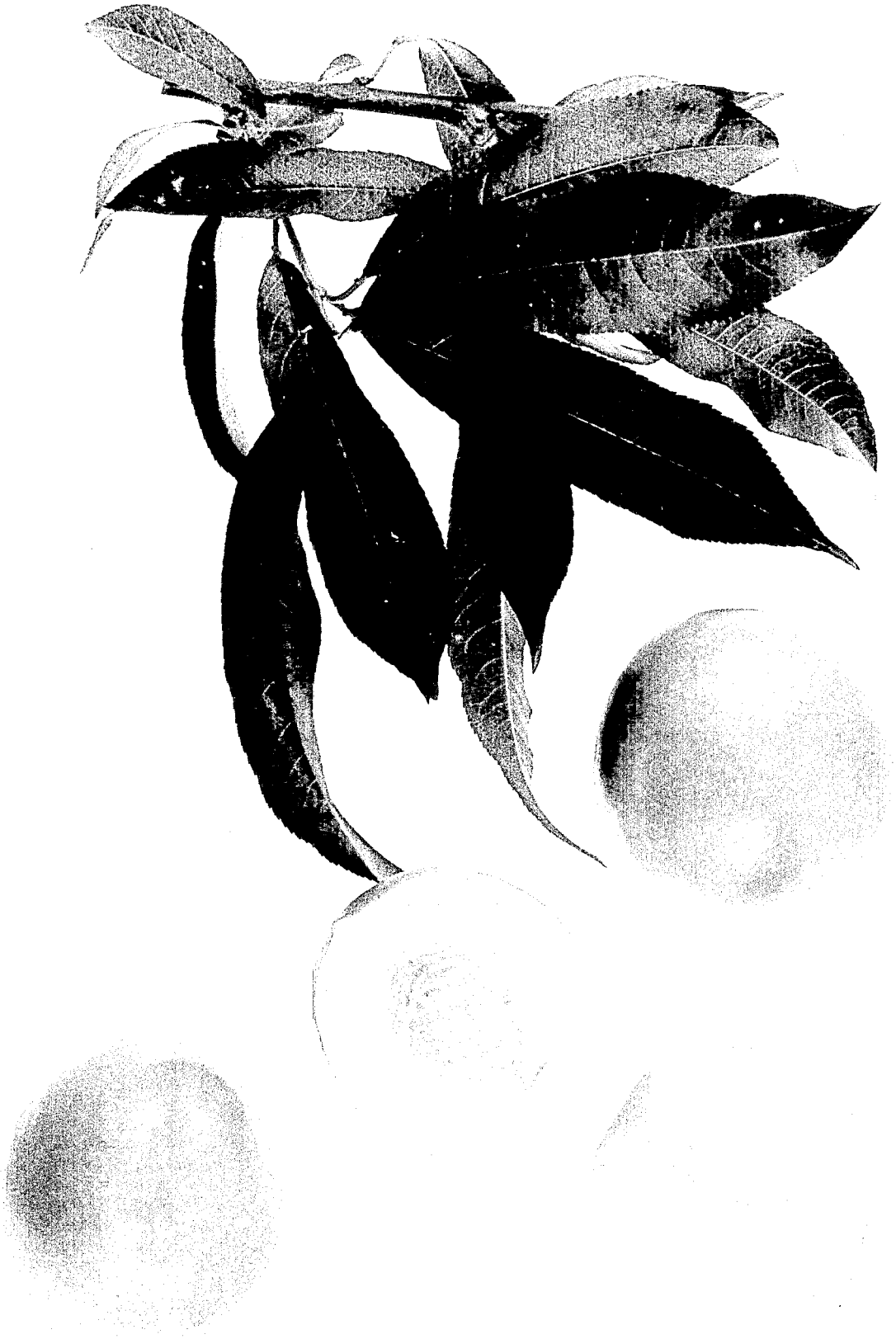

U.S. Patent Apr. 25, 1989 Plant 6,753